United States Patent [19]

Chiang et al.

[11] Patent Number: 4,981,949

[45] Date of Patent: Jan. 1, 1991

[54] METHOD FOR POLYMERING AROMATIC HETEROCYCLIC COMPOUNDS

[75] Inventors: Long Y. Chiang, Somerset; Russell R. Chianelli, Somerville, both of N.J.; John W. Swirczewski, Kintnersville, Pa.

[73] Assignee: Exxon Research and Engineering Company, Florham Park, N.J.

[21] Appl. No.: 519,961

[22] Filed: May 7, 1990

Related U.S. Application Data

[62] Division of Ser. No. 307,452, Feb. 8, 1989, Pat. No. 4,971,983.
[51] Int. Cl.$^5$ ............................................ C08F 134/00
[52] U.S. Cl. .................................................... 528/423
[58] Field of Search ......................................... 528/423

[56] References Cited

U.S. PATENT DOCUMENTS 4,727,135 2/1988 Chiang et al. ..................... 528/423

Primary Examiner—Joseph L. Schofer
Assistant Examiner—M. Nagumo
Attorney, Agent, or Firm—Joseph J. Dvorak

[57] ABSTRACT

The present invention includes a composition of matter comprising a sulfide of a metal selected from Groups VIB, VIIB and VIII of the Periodic Tables, or mixtures thereof, and an aromatic, nitrogen-containing heterocyclic compound selected from the group consisting of tetrahydroquinoline, and the mono and diorgano substituted derivatives of tetrahydroquinoline. These compositions are useful as catalyst precursors. Indeed, upon heating at temperatures above 200° C., the compounds are converted to active catalysts useful in polymerizing nitrogen-containing heterocyclic compounds.

4 Claims, No Drawings

METHOD FOR POLYMERING AROMATIC HETEROCYCLIC COMPOUNDS

This is a division of application Ser. No. 307,452 filed Feb. 8, 1989 now U.S. Pat. No. 4,971,938.

FIELD OF THE INVENTION

This invention relates to organic amine-containing metal sulfide compositions. Also, this invention relates to methods for their preparation. Finally, this invention relates to use of the organic amine-containing metal sulfide compositions as catalysts in the dehydrogenative polymerization of nitrogen-containing heterocyclic compounds like tetrahydroquinoline.

BACKGROUND OF THE INVENTION

In U.S. Pat. No. 4,727,135 there is described a method for polymerizing certain aromatic nitrogen-containing heterocyclic compounds using a metal sulfide catalyst in which the metal is selected from the group consisting of transition metals of Group VIB, VIIB and VIII of the Periodic Table or mixtures thereof. The preferred catalyst for the polymerization of the aromatic, nitrogen-containing heterocyclic compounds is reported to be rhenium sulfide, $ReS_{2+x}$.

In *Catalyst Letters*, 1, 177 to 182 (1988), two soluble rhenium complexes are reported to be useful in generating rhenium sulfides that are catalytically active in the dehydrogenative polymerization of 1,2,3,4-tetrahydroquinoline.

We now have discovered a new series of organic amine-containing metal sulfide compounds that are particularly suitable as catalysts for the dehydrogenative polymerization of aromatic, nitrogen-containing heterocyclic compounds like tetrahydroquinoline.

SUMMARY OF THE INVENTION

One embodiment of the present invention encompasses a composition of matter comprising a sulfide of a metal selected from Groups VIB, VIIB, VIII of the Periodic Table, and mixtures thereof, and an aromatic, nitrogen-containing heterocyclic compound selected from the group consisting of tetrahydroquinoline and the mono and diorgano-substituted derivatives of tetrahydroquinoline. The organo substituent in the mono and diorgano-substituted derivatives is selected from alkyl groups having from 1 to 20 carbon atoms, aryl groups having from about 6 to 25 carbon atoms, alkoxyl groups having from 1 to 20 carbon atoms, alkylamino groups having from 1 to 30 carbon atoms, aryloxy groups having from 6 to 25 carbon atoms, and arylamino groups having from 6 to 25 carbon atoms. These compositions are useful as catalyst precursors. Indeed, upon heating at elevated temperature, for example, at temperatures above about 200° C., these compounds are converted to active catalyst useful in the dehydrogenative polymerization of aromatic, nitrogen-containing heterocyclic compounds.

Another embodiment of the present invention encompasses a process for preparing organic amine-containing metal sulfides comprising contacting a chloride of a metal selected from Groups VIB, VIIB, or VIII of the Periodic Table of the Elements, or mixtures thereof, with hydrogen sulfide in the presence of an aromatic, nitrogen-containing heterocyclic compound selected from the group consisting of tetrahydroquinoline and the mono and diorgano-substituted derivatives of tetrahydroquinoline in an amount and for a time sufficient to convert the chloride to the organic amine-containing metal sulfide. The organo substituent in the heterocyclic compounds is selected from alkoxyl groups having from 1 to 20 carbon atoms, alkylamino groups having from 1 to 30 carbon atoms, aryloxy groups having from 6 to 25 carbon atoms, and arylamino groups having from 6 to 25 carbon atoms.

The present invention also encompasses an improved method of polymerizing at least one aromatic nitrogen-containing heterocyclic compound like tetrahydroquinoline.

DETAILED DESCRIPTION OF THE INVENTION

The compositions of the present invention comprise a sulfide of a metal selected from Groups VIB, VIIB and VIII of the Periodic Table of the Elements, and mixtures thereof, and an aromatic, nitrogen-containing heterocyclic compound selected from the group consisting of tetrahydroquinoline and the mono and diorgano-substituted derivatives of tetrahydroquinoline.

The Periodic Table of the Elements referred to herein is that found inside the cover of Lang's Handbook of Chemistry, 11th Edition, McGraw Hill, Inc., (1973). Preferably, the metal in the compositions of the present invention is selected from Ni, Co, Re, Ru, Mo, Rh, Pd and Pt.

Examples of suitable nitrogen-containing heterocyclic compounds include 1,2,3,4-tetrahydroquinoline, 3-monoorgano-substituted 1,2,4-trihydroquinoline, 4-monoorgano-substituted 1,2,3-trihydroquinoline, 5-monoorgano-substituted 1,2,3,4-tetrahydroquinoline, 7-monoorgano-substituted 1,2,3,4-tetrahydroquinoline, 8-monoorgano-substituted 1,2,3,4-tetrahydroquinoline, 4, 8-diorgano-substituted 1,2,3-trihydroquinoline, 4, 5-diorgano-substituted 1,2,3-trihydroquinoline, and 7, 8-diorgano-substituted 1,2,3,4-tetrahydroquinoline. The organo substituent in the mono and diorgano-substituted compounds listed above is selected from alkyl groups having from 1 to 20 carbon atoms, aryl groups having from about 6 to 25 carbon atoms, alkoxyl groups having from 1 to 20 carbon atoms, alkylamino groups having from 1 to 30 carbon atoms, aryloxy groups having from 6 to 25 carbon atoms, and arylamino groups having from 6 to 25 carbon atoms.

The ratio of the aromatic, nitrogen-containing heterocyclic compound to metal sulfide in these compounds is in the range of about 0.2:1 to about 2:1.

The compositions of the present invention are prepared by contacting a Group VIB, VIIB or VIII metal halide, ammonium metal halide, or mixtures thereof with hydrogen sulfide in the presence of an aromatic, nitrogen-containing heterocyclic compound. The ratio of aromatic, nitrogen-containing heterocyclic compound to metal halide, ammonium metal halide or mixtures thereof will be at least 1:1 and preferably a large excess of heterocyclic compound is employed. Indeed, it is particularly preferred to carry out the contacting using the aromatic, nitrogen-containing heterocyclic compound as a solvent.

The amount of hydrogen sulfide employed will be sufficient to convert the metal halide or ammonium metal halide to a sulfide, and generally excess hydrogen sulfide is employed.

Because the aromatic, nitrogen-containing heterocyclic metal sulfide compounds of the present invention are generally insoluble in non-polar solvents, these compounds can be isolated by filtration from such solvent systems. For example, if 1,2,3,4-tetrahydroquinoline is employed as a solvent and rhenium pentachloride is used as the metal chloride of choice, a solution of rhenium pentachloride and tetrahydroquinoline can be conveniently contacted with excess hydrogen sulfide, for example, by bubbling the hydrogen sulfide through the solution. This results in the formation of a suspension of the tetrahydroquinoline-containing rhenium sulfide. The addition of a non-polar solvent, such as hexane, will complete the precipitation of the tetrahydroquinoline-containing rhenium sulfide which is then readily separated by filtration.

The compositions of this invention are converted to active catalysts by heating them at elevated temperatures in an inert atmosphere for a time sufficient to convert the catalyst precursors to the active catalyst. The heating time is not critical and in general will range from about 20 minutes to about 3 hours. The temperature employed will generally be above about 200° C. and preferably in the range of about 210° C. to about 270° C.

Alternatively and preferably, a suspension of the aromatic, nitrogen-containing heterocyclic metal sulfide compounds may be employed in situ for the dehydrogenative polymerization of the aromatic, nitrogen-containing heterocyclic compounds.

Basically, the dehydrogenation polymerization process of the present invention comprises heating the aromatic, nitrogen-containing heterocyclic compound in the presence of the aromatic, nitrogen-containing metal sulfide for a time sufficient to polymerize the aromatic, nitrogen-containing heterocyclic compound. In general, the heating will be at the boiling point of the heterocyclic compound. Preferably, the polymerization will be conducted at reflux temperature of the heterocyclic compound or 270° C., whichever is lower. In general, heating will be at atmospheric pressures and in an inert atmosphere such as a nitrogen or argon atmosphere.

The polyquinoline polymers formed in the process of this invention are represented by the general formula:

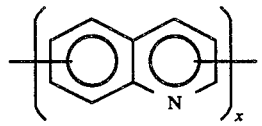

in which x is an integer $\geq 2$.

To further illustrate the present invention, reference is made to the following Examples in which, for convenience, THQ shall mean 1,2,3,4-tetrahydroquinoline.

EXAMPLES

Example 1—Synthesis of THQ-Containing Rhenium Sulfide Complex

In this example, a 3 neck flask connected with a condenser having a hydrogen inlet tube was charged with 400 grams of dried THQ which was maintained under a nitrogen atmosphere. Then rhenium pentachloride (17.4 grams, 48 millimoles) was slowly added to the THQ over a period of 4 hours to prevent a rise of the temperature above 80° C. The mixture was stirred for an additional 8 hours and then was purged below the liquid surface with hydrogen sulfide for 4 hours at a flow rate of 20 ml/minute. The mixture was then stirred for about 12 hours at ambient temperature. The resultant suspension was a THQ-containing rhenium sulfide.

To isolate and further identify the THQ-containing metal sulfide, the suspension was added to 1 liter of n-hexane, and then filtered under vacuum and washed with 200 ml of hexane, 500 ml of water and then 400 ml of acetone. It was then dried under vacuum at 50° C. to yield a THQ-containing rhenium sulfide in which the THQ to Re ratio was about 2:1. Elemental analysis is as follows: C, 30.01; H, 2,50; N, 4.00; S, 15.53; Cl, 9.73; Re, 26.44. The analysis corresponds to a composition $(THQ)_2 ReS_{3.5} Cl_{1.9}$.

Example 2—Synthesis of THQ-Containing Ruthenium Sulfide Complex

The procedure of Example 1 was followed, except that ammonium hexachloryl ruthenate (16.8 grams, 48 milliliters) was used in lieu of the rhenium pentachloride. Elemental analysis of the dried, isolated product is as follows: C, 24.77; H, 3.48; N, 8.03; S, 18.91; Cl, 15.10; Ru, 20.58. This corresponds to a THQ to Ru ratio of 1.1:1.

Example 3—Synthesis of THQ-Containing Rhodium Sulfide Complex

The procedure of Example 1 was followed, except that rhodium dichloride (10 grams, 48 millimoles) was employed instead of the rhenium pentachloride. The isolated solid had the following elemental analysis: C, 13.54; H, 1.96; N, 1.88; S, 30.72; Cl, 5.33; Rh, 32.60. This corresponds to a THQ to Rh ratio of 0.4:1.

Example 4—Synthesis of THQ-Containing Molybdenum Sulfide

In this example, the procedure of Example 1 was employed except that molybdenum pentachloride (13.1 grams, 48 millimoles) was used instead of rhenium pentachloride. Elemental analysis for the isolated product is as follows: C, 29.70; H, 3.15; N, 4.13; S, 16.24; Cl, 10.56; Mo, 26.28. This corresponds to a THQ to Mo ratio of 1.1 to 1.

Example 5—Synthesis of THQ-Containing Molybdenum Sulfide/Nickel Sulfide Complex This example illustrates the preparation of a mixed metal sulfide composition containing THQ. The procedure of Example 1 was followed except that a mixture of molybdenum pentachloride (9.84 grams, 36 millimoles) and nickel chloride (1.6 grams, 12 millimoles) was used in lieu of the rhenium pentachloride. Elemental analysis of the isolated product is as follows: C, 26.87; H, 3.19; N, 3.66; S, 12.36; Cl, 17.60; Mo, 20.42; Ni, 1.24. This corresponds to a THQ to total metal ratio of about 1.1:1.

Example 6—Procedure for Synthesis of Polyquinoline

Multiple runs were conducted using the catalysts prepared in Examples 1 to 5. In each run a single neck, round bottomed flask equipped with a condenser and an inert gas bubbler was charged with a suspension of the THQ-containing metal sulfide. The suspended mixture was maintained under an argon atmosphere and heated at 270° C. for from 15 to about 21 hours. At this temperature, a gentle reflux of tetrahydroquinoline was obtained. At the end of the reaction, the resulting product was cooled to room temperature to give a dark solid. The mixture was added to chloroform (2.5 liters) to form a suspension which was stirred overnight at room temperature. The insoluble solid was then filtered and washed with another portion of chloroform (400 ml). The chloroform solution was then evaporated to give a dark reddish-brown paste, which was suspended and stirred in diethylether (2 liters) for 8 hours. The insolubles were filtered and washed with diethylether (200 ml), to yield a brown solid product fraction, PQC, which was chloroform-soluble and diethylether-insoluble. The solvent of the combined diethylether filtrates was evaporated to give a reddish sludge, which was then suspended and stirred in hexane (2 liters) for 8 hours. The insoluble solid was filtered and washed with hexane (200 ml) to yield a product fraction, PQB, which is diethylether-soluble and hexane-insoluble. The remaining hexane-solubles were dried to give a product fraction, PQA. The chloroform-insolubles from the first solvent extraction were subsequently treated with concentrated HCl and stirred overnight. The resulting acid solution was filtered through a sintered glass frit with a diatomaceous earth filter agent sold under the trademark, Celite by Johns Manville Products, Manville, N.J. The filtrate was neutralized with aqueous NaOH to effect the precipitation of a gray solid product fraction, referred to as PQD. The ratios of the various products are given in the following table:

TABLE I

| Run | Catalyst | PQA, wt % | PQB, wt % | PQC, wt % | PQD, wt % |
|---|---|---|---|---|---|
| 1 | Ex 1 | 16 | 0 | 43 | 41 |
| 2 | Ex 2 | 7 | 11 | 34 | 48 |
| 3 | Ex 3 | 6 | 8 | 36 | 50 |
| 4 | Ex 4 | 6 | 13 | 42 | 39 |
| 5 | Ex 5 | 0 | 12 | 64 | 24 |

Elemental analyses of products in all of these fractions were consistent with a molecular formulation of $C_9H_{5+x}N$ close to the expected polyquinoline composition in which the value of x varies as a function of both the degree of aromatization and polymerization; the characterization of products was based mainly on the PQC fraction isolated from the bulk product. The mass spectrum (electron impact) of the tetrameric quinoline isolated from the PQC fraction shows a clear consecutive weight loss of 127 which corresponds to the mass of a quinoline unit in the oligomer. It also shows ion fragmentations of 128,255,383,510, etc., corresponding to the monomeric, dimeric, trimeric, and tetrameric quinoline fragments. Infrared spectrum of all quinoline oligomer fractions compared with that of 1,2,3,4-tetrahydroquinoline itself, showed a new band at 821 cm$^{-1}$ corresponding to the C—H out-of-plane deformation of heterocyclic ring moiety of quinoline in addition to a band at 746 cm$^{-1}$ of the C—H out-of-plane deformation of benzene ring moiety of quinoline. This, along with the disappearance of a N—H band and a band at 2800-2930 cm$^{-1}$ in the IR spectrum of oligomer, which corresponds to the aliphatic C—H stretch in THQ, indicated that the heterocyclic ring moiety of oligomer has been fully dehydrogenated.

The high aromaticity of the oligomer was further confirmed by the NMR spectroscopy. Both $^1$H NMR and $^{13}$C NMR of the oligomer fraction PQD contained either no, or only a trace of, aliphatic hydrogen and aliphatic carbon signals. The most characteristic peaks in the proton NMR were three peaks above 8.8 ppm. Two of them centered at 9.58 ppm and 8.88 ppm corresponding to two kinds of α proton adjacent to the nitrogen atom in the quinoline unit as an end group. These two α protons show a similar range of chemical shift as that of the α proton of 2,3'-biquinoline (δ 9.72) and 2,6'-biquinoline (δ 8.95), which are the only two dimers isolated from the bulk product by chromatography. The third peak centered at 8.82 ppm was found to be in the similar chemical shift range of proton H$_{4'}$ (δ 8.84) of 2,3'-biquinoline. Since this fraction contains no dimers, it clearly implies that the structural environment of α protons in oligomers is closely related to that of dimers 2,3'-biquinoline and 2,6'-biquinoline.

The PQB fraction mainly contains a partially hydrogenated quinoline oligomer and quinoline dimer with a small amount of trimer.

What is claimed is:

1. A method of polymerizing an aromatic, nitrogen-containing heterocyclic compound selected from the group consisting of tetrahydroquinoline, monoorgano-substituted tri or tetrahydroquinolines, and diorgano-substituted tri or tetrahydroquinolines comprising heating the compound selected at elevated temperatures and in the presence of a catalyst formed by heating a catalyst precursor at a temperature above about 200° C., the precursor being a compound containing a metal sulfide of Group VIB, VIIB, and VIII metals or mixtures thereof and an aromatic, nitrogen-containing heterocyclic compound selected from tetrahydroquio-line, monoorgano-substituted tri or tetrahydroquino-lines, and diorgano-substituted tri or tetrahydro-quinolines, said organo substituents being selected from alkyl groups having from 1 to 20 carbon atoms, aryl groups having from about 6 to 25 carbon atoms, alkoxyl groups having from 1 to 30 carbon atoms, aryloxy groups having from 6 to 25 carbon atoms, and arylamino groups having from 6 to 25 carbon atoms.

2. The method of claim 1 wherein the heating of the compound selected is at temperatures ranging from about 210° C. to 270° C.

3. The method of claim 2 wherein the heterocyclic compound selected is tetrahydroquinoline.

4. The method of claim 2 wherein the compound selected and the catalyst precursor are heated together.

* * * * *